United States Patent
Eleftherou et al.

(10) Patent No.: US 11,694,800 B2
(45) Date of Patent: Jul. 4, 2023

(54) MEDICAL DIAGNOSIS SYSTEM WITH CONTINUOUS LEARNING AND REASONING

(71) Applicant: International Business Machines Corporation, Armonk, NY (US)

(72) Inventors: Maria Eleftherou, Mount Kisco, NY (US); Chung-Sheng Li, Scarsdale, NY (US); Shahram Ebadollahi, White Plains, NY (US); Francisco Curbera, Hastings On Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 405 days.

(21) Appl. No.: 15/975,046

(22) Filed: May 9, 2018

(65) Prior Publication Data
US 2019/0348178 A1 Nov. 14, 2019

(51) Int. Cl.
*G16H 50/20* (2018.01)
*G16H 50/50* (2018.01)
(Continued)

(52) U.S. Cl.
CPC ........... *G16H 50/20* (2018.01); *G06N 20/00* (2019.01); *G16H 10/60* (2018.01); *G16H 50/50* (2018.01);
(Continued)

(58) Field of Classification Search
None
See application file for complete search history.

(56) References Cited

U.S. PATENT DOCUMENTS

| 7,379,885 B1 | 5/2008 | Zakim |
| 8,521,556 B2 | 8/2013 | Chbat et al. |

(Continued)

FOREIGN PATENT DOCUMENTS

| WO | WO-2008103827 A1 * | 8/2008 | ............. G16H 10/60 |
| WO | WO-2013077977 A1 * | 5/2013 | ............ G06F 19/328 |

(Continued)

OTHER PUBLICATIONS

Stern CR, Luger GF. Abduction and abstraction in diagnosis: a schema-based account. J. Expertise in context. May 30, 1997:363-81. (Year: 1997).*

(Continued)

*Primary Examiner* — Rachel L. Porter
(74) *Attorney, Agent, or Firm* — Patterson + Sheridan, LLP

(57) ABSTRACT

Performing an operation comprising generating, by a computing system based on data received from a plurality of data sources, a data model describing a patient, wherein the data comprises medical history data of the patient and observation data received by the computing system during observation of at least one medical professional, generating, by the computing system and based on the model applied to the received data, a plurality of candidate diagnoses for the patient, executing, by the computing system, a plurality of simulations of a plurality of candidate treatments generated by the computing system based on the model, and identifying a first candidate treatment of the plurality of candidate treatments that reduces an uncertainty value of the data model below a threshold.

20 Claims, 8 Drawing Sheets

(51) Int. Cl.
  *G16H 10/60* (2018.01)
  *G06N 20/00* (2019.01)
  *G16H 70/20* (2018.01)
  *G16H 10/40* (2018.01)
  *G16H 80/00* (2018.01)
  *G16H 50/30* (2018.01)

(52) U.S. Cl.
  CPC ............ *G16H 10/40* (2018.01); *G16H 50/30* (2018.01); *G16H 70/20* (2018.01); *G16H 80/00* (2018.01)

(56) References Cited

U.S. PATENT DOCUMENTS

| | | |
|---|---|---|
| 2006/0292535 A1 | 12/2006 | O'Connor et al. |
| 2008/0015894 A1 | 1/2008 | Miller et al. |
| 2012/0047105 A1* | 2/2012 | Saigal ............ G16Z 99/00 706/52 |
| 2012/0197619 A1* | 8/2012 | Namer Yelin ........ G16H 50/50 703/11 |
| 2014/0122109 A1* | 5/2014 | Ghanbari ............ G16H 10/20 705/2 |
| 2014/0279746 A1* | 9/2014 | De Bruin ............ A61B 5/7267 706/12 |
| 2015/0169833 A1 | 6/2015 | Waltinger et al. |
| 2015/0242583 A1 | 8/2015 | Edson |
| 2015/0331997 A1* | 11/2015 | Joao .................. G16H 10/60 705/3 |
| 2015/0359601 A1* | 12/2015 | Sauer .................. G06K 9/6256 382/128 |
| 2016/0078182 A1* | 3/2016 | Allen .................. G16H 50/20 702/19 |
| 2016/0171383 A1* | 6/2016 | Narain ................ G06N 7/005 706/52 |
| 2017/0249434 A1* | 8/2017 | Brunner ............. G06F 16/258 |
| 2017/0308671 A1* | 10/2017 | Bahrami ............. G16H 10/60 |
| 2018/0225424 A1* | 8/2018 | Kaditz ................. G16H 50/20 |
| 2018/0247020 A1* | 8/2018 | Itu ....................... G16H 10/60 |
| 2018/0344919 A1* | 12/2018 | Jones .................. G16H 50/50 |
| 2018/0357359 A1* | 12/2018 | Markovic ............ G16B 40/00 |
| 2019/0198179 A1* | 6/2019 | Dey ..................... G16H 20/10 |
| 2019/0326016 A1* | 10/2019 | Kent .................... G16H 50/30 |
| 2020/0098477 A1* | 3/2020 | Peták .................. G16H 50/70 |

FOREIGN PATENT DOCUMENTS

| | | | | |
|---|---|---|---|---|
| WO | WO-2014117873 A1 | * | 8/2014 | ............. G06F 19/18 |
| WO | WO-2016187321 A1 | * | 11/2016 | ............. G16H 50/50 |

OTHER PUBLICATIONS

Yuan Luo, "Recurrent neural networks for classifying relations in clinical notes", Journal of Biomedical Informatics, vol. 72, pp. 85-95. (Year: 2017).*

L. Oberste and A. Heinzl, "User-Centric Explainability in Healthcare: A Knowledge-Level Perspective of Informed Machine Learning," IEEE Transactions on Artificial Intelligence, Dec. 6, 2022, pp. 1-18 (doi: 10.1109/TAI.2022.3227225 (Year: 2022).*

* cited by examiner

MEDICAL DIAGNOSIS SYSTEM WITH CONTINUOUS LEARNING AND REASONING

BACKGROUND

The present invention relates to computing systems, and more specifically, to medical diagnosis systems that apply continuous learning and reasoning.

Generating medical diagnoses is often challenging because many patient signs and symptoms are nonspecific. For example, redness of the skin is a sign of many disorders, and cannot be used in isolation to diagnose an illness. Therefore, differential diagnosis, in which several possible diagnoses are compared and contrasted, must be performed. Furthermore, clinical diagnosis systems often generate substantial errors in the form of false positive and false negative diagnoses. In spite of the need for to improve these errors, conventional techniques to improve clinical diagnosis systems have provided limited improvements.

SUMMARY

According to one embodiment, a method comprises generating, by a computing system based on data received from a plurality of data sources, a data model describing a patient, wherein the data comprises medical history data of the patient and observation data received by the computing system during observation of at least one medical professional, generating, by the computing system and based on the model applied to the received data, a plurality of candidate diagnoses for the patient, executing, by the computing system, a plurality of simulations of a plurality of candidate treatments generated by the computing system based on the model, and identifying a first candidate treatment of the plurality of candidate treatments that reduces an uncertainty value of the data model below a threshold.

In another embodiment, a system comprises a processor and a memory storing instructions, which when executed by the processor, performs an operation comprising generating, by the system based on data received from a plurality of data sources, a data model describing a patient, wherein the data comprises medical history data of the patient and observation data received by the system during observation of at least one medical professional, generating, by the system and based on the model applied to the received data, a plurality of candidate diagnoses for the patient, executing, by the computing system, a plurality of simulations of a plurality of candidate treatments generated by the system based on the model, and identifying a first candidate treatment of the plurality of candidate treatments that reduces an uncertainty value of the data model below a threshold.

In another embodiment, a computer-readable storage medium has computer-readable program code embodied therewith, the computer-readable program code executable by a processor to perform an operation comprising generating, by a computing system based on data received from a plurality of data sources, a data model describing a patient, wherein the data comprises medical history data of the patient and observation data received by the computing system during observation of at least one medical professional, generating, by the computing system and based on the model applied to the received data, a plurality of candidate diagnoses for the patient, executing, by the computing system, a plurality of simulations of a plurality of candidate treatments generated by the computing system based on the model, and identifying a first candidate treatment of the plurality of candidate treatments that reduces an uncertainty value of the data model below a threshold.

DETAILED DESCRIPTION

Embodiments disclosed herein provide a medical diagnosis system which continuously learns based on different data sources, including medical history data, clinical studies, and live settings where medical professionals interact with patients and colleagues. The medical diagnosis system is initially configured with high-quality explicit training to generate one or more models. The models may generally be used to generate candidate diagnoses and/or candidate treatments for patients. In at least one embodiment, the models include a two-level learning model. After the explicit training, the medical diagnosis system learns new features by following and interacting with real medical professionals and patients. The medical diagnosis system continuously updates the diagnosis of a patient based on existing disease models and reasoning as new information about the patient is received. Simultaneously, the underlying diagnosis model is updated through reinforcement learning, capturing the experience of every encounter by the system with patients and/or medical professionals. By using deep learning, abduction reasoning, and reinforcement learning algorithms, the medical diagnosis systems disclosed herein achieve improved performance in diagnosing patients and generating candidate treatments across any number of medical domains. Furthermore, by allowing the medical diagnosis system to observe medical professionals, test results, and the like, the medical professionals need not provide explicit input to train the medical diagnosis system.

Figure 1:
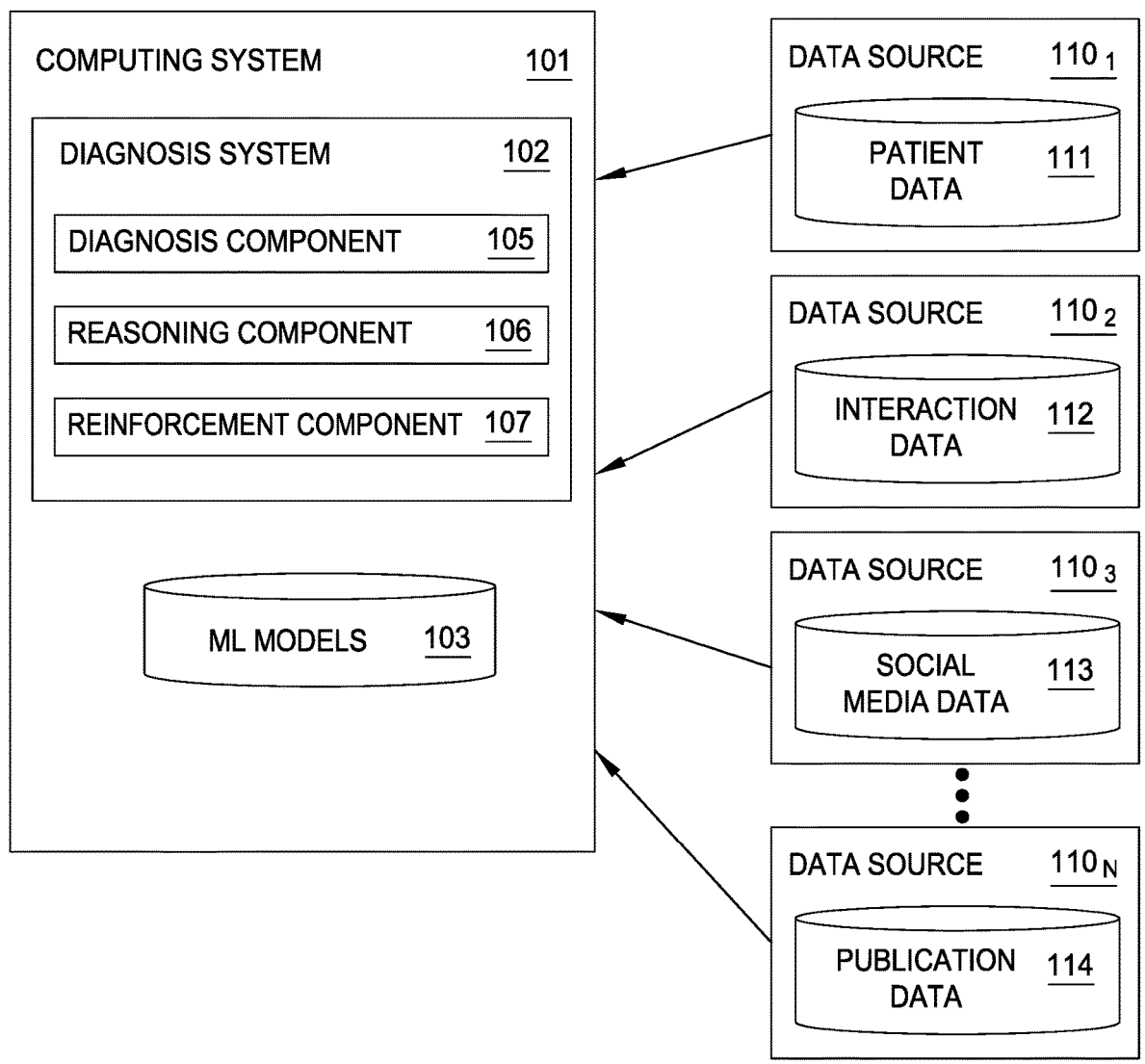
FIG. 1 illustrates a medical diagnosis system configured to perform continuous learning and reasoning, according to one embodiment.

FIG. 1 illustrates a medical diagnosis system 100 configured to perform continuous learning and reasoning, according to one embodiment. As shown, the system 100 includes a computing system 101 and a plurality of data sources $110_{1-N}$. The computing system 101 includes a diagnosis system 102 and one or more models 103. The diagnosis system 102 is generally configured to generate candidate diagnoses and/or treatments for patients based on continuous learning and reasoning. Generally, the diagnosis system 102 generates a data model for a patient based on the patient's medical history, where the model is associated with some level of uncertainty. The diagnosis system 102 may then emulate a plurality of "what-if" scenarios by applying treatments having known effects to the patient, where the patient is associated with a set of observed conditions. The emulation may further include emulating the treatments and generating an uncertainty measure relative to an unknown future model of the patient (e.g., the patient's condition in the future). The diagnosis system 102 may then generate a treatment option that minimizes the uncertainty measure and to improve the adjusted risk outcome for the patient. Further still, the diagnosis system 102 updates the data model of the patient using reinforcement learning based on the results of the emulation and the generated treatment option.

The diagnosis system 102 includes a diagnosis component 105, a reasoning component 106, and a reinforcement component 107. The diagnosis component 105 is representative of a closed-loop system that receives data describing a patient, generates a model 103 for the patient including a diagnosis for the patient, emulates the potential outcomes of different treatments, and selects the best treatment for a diagnosed condition. The "best" treatment may be the treatment that minimizes the uncertainty of the patient model 103 (e.g., reduces the uncertainty below a threshold uncertainty value). The diagnosis component 105 may refine and/or change the treatment over time as the patient is treated, e.g., if a first treatment does not work as desired, the diagnosis component 105 may generate a second treatment for a patient based on the model 103. The reasoning component 106 is configured to apply abduction reasoning to generate hypotheses that can explain known observations, e.g., to generate candidate diagnoses and/or treatments based on a patient's state. The reasoning component 106 may update the models 103 using abductive reasoning. The reinforcement component 107 applies reinforcement learning to revise the models 103 by increasing the accuracy and/or reducing the uncertainty of each model.

The models 103 are data models that include patient state models as well as underlying diagnosis models. The patient state models store data describing the state of one or more patients, and are generated based on data describing the patient received from the data sources $110_{1-N}$. As used herein, a "model" refers to any type of data model, such as machine learning (ML) models, neural networks, decision trees, classifiers, and the like. Illustratively, the data sources $110_{1-N}$ include patient data 111, interaction data 112, social media data 113, and publication data 114. The types and/or formats of data in the data sources $110_{1-N}$ should not be considered limiting of the disclosure, as any type of data may be leveraged by the diagnosis system 102. The patient data 111 includes data describing a plurality of patients, including without limitation, electronic health records, lab tests, scans, observed parameters, disorders, diseases, and the like. The patient data 111 may include historical data as well as data observed in real time. The interaction data 112 is representative of data observed by the diagnosis system 102 while interacting with medical professionals, such as audio recordings of a doctor speaking to residents captured by a microphone of the computing system 101, clinical notes written by the doctor, images captured by a camera of the computing system, and the like. The social media data 113 is representative of data received from social media platforms, blogs, and the Internet in general. The publication data 114 is representative of high-quality scholarly articles, publications, experiments, dictionaries, ontologies, knowledge graphs, knowledge bases, and the like. In at least one embodiment, the models 103 are further trained based on the knowledge bases, and the diagnosis system 102 and/or the models 103 may leverage the knowledge bases to generate candidate diagnoses and/or candidate treatments for a given patient.

Returning to the models 103, the state of a patient described in the models 103 may generally include a plurality of different attributes of the patient. In one embodiment, the state of the patient includes a concepts dimension, a type dimension, a stage dimension, and a scope dimension. The concepts dimension include patient attributes such as diseases, illnesses, disorders, medical conditions, morbidity, syndromes, and predisease conditions. The types dimension may include an indication of the type of each condition, such as whether a condition is mental, organic, etc. The stages dimension describes a stage of a condition, such as acute disease, chronic disease, flare-up, refractory disease, progressive disease, a cured disease, clinical disease, subclinical disease, etc. The scope dimension reflects the scope of a condition, such as a localized disease, disseminated disease, and a systemic disease. The patient models in the models 103 may therefore include a time series of vectors, where each vector captures attributes of the patient for each of the foregoing dimensions. In at least one embodiment, the diagnosis component 105 generates the models 103 based on one or more learning algorithms (e.g., machine learning algorithms, etc.) applied to the data describing the patient attributes and. As such, the models 103 may include an associated uncertainty measure, and the diagnosis system 102 may need to determine the current state of a patient through abduction reasoning and/or differential diagnosis performed by the reasoning component 106 to produce the most likely diagnoses to describe the current state of the patient.

The diagnosis component 105 may generally leverage the models 103 to determine one or more candidate diagnoses for a patient, as well as one or more candidate treatments for each candidate diagnosis. The diagnosis component 105 and/or the reasoning component 106 may further perform simulations and predictions for each candidate diagnosis and candidate treatment to evaluate the risks and possible outcomes of each diagnosis and/or treatment. Generally, the diagnosis component 105 and/or reasoning component 106 may consider the model 103 of the patient, interactions with medical professionals, knowledge bases, test results, and the like, to converge on a candidate diagnosis for the patient that minimizes the uncertainty of the model 103 for the patient at some time in the future. Similarly, the diagnosis component 105 and/or reasoning component 106 may consider the candidate diagnosis, the model 103 of the patient, interactions with medical professionals, knowledge bases, etc., to generate a plurality of candidate treatments, and simulate each treatment for the patient.

For example, if surgery is generated as candidate treatment for a generated diagnosis, the diagnosis component 105 may consider the discordance rate between the clinical diagnosis of other patients and the outcomes of the treatments for the other patients in the patient data 111 during a plurality of simulations of surgery as the treatment. For example, if the patient data 111 indicates that 55% of the patients who had surgery for a given diagnosis did not have a successful outcome, the diagnosis component 105 may consider the success rates in simulating the treatment, and revise the treatment plans accordingly.

In at least one embodiment, the diagnosis component 105 and/or the reasoning component 106 may generate one or more candidate diagnoses, and compute a score for each candidate diagnosis. The computed score reflects a degree of confidence that each diagnosis is correct and/or reduces the uncertainty measure associated with the model 103 of the patient. The medical professional may then select a candidate diagnosis for a patient, and may optionally provide feedback altering the candidate diagnoses computed by the diagnosis component 105 and/or the reasoning component 106. The medical professional may then select a candidate treatment for a patient, and may optionally provide feedback altering one or more candidate treatment plans computed by the diagnosis component 105 and/or the reasoning component 106.

For example, the diagnosis component 105 may determine based on a medical health record in the patient data 111 that a patient's symptoms include hip pain, while the interaction data 112 includes an audio recording of a medical professional stating that the patient is mentally unstable and non-cooperative. Lab results in the patient data 111 may indicate that the patient's kidneys are not functioning properly, and the patient's potassium levels are elevated. Similarly, the patient data 111 include an ultrasound result indicating that the patient's bladder is blocked. Based on the received data, the diagnosis component 105 may refine the model 103 for the patient to include a current time vector for the patient describing the above attributes as well as any other attributes of the patient. Based on the model 103 for the patient, underlying disease models, and other data received regarding the patient (e.g., a medical professional's initial diagnosis and/or treatment), the diagnosis component 105 may generate one or more candidate diagnoses. The reasoning component 106 may also generate candidate diagnoses based on abduction reasoning applied to the patient state data in the models 103.

Based on the candidate diagnoses, data received from the data sources $110_{1-N}$, and the models 103, the diagnosis component 105 and/or the reasoning component 106 may further generate and refine one or more candidate treatment plans for each candidate diagnosis. The diagnosis component 105 and/or the reasoning component 106 generate candidate treatment plans that optimize the risk adjusted outcome for the patient, and identify the additional data observations (e.g., lab tests, patient state attributes, etc.) that are needed to reduce the uncertainty of the patient's state model, and improve the accuracy of the models 103. The diagnosis system 102 may then output the candidate diagnoses, candidate treatment plans, and the additional data needed to a medical professional for review. The medical professional may then select one or more candidate diagnoses, treatments, and additional data observations, which are stored for later use. In at least one embodiment, the diagnosis system 102 is configured to ask questions of the medical professional (e.g., to discuss the additional data needed, etc.) who may then provide responses as interaction data 112. As stated, the diagnosis component 105 and/or the reasoning component 106 may continue to develop and revise the diagnosis, treatment plans, and additional observations needed as additional data for each patient is observed (e.g., whether the patient improves, updated lab results, new statements observed from a medical professional from the interaction data 112). For example, for the above described patient, the diagnosis component may determine that the patient has metastatic prostate cancer, which is ultimately confirmed by a biopsy in the patient data 111.

The reinforcement component 107 applies reinforcement learning to continuously revise the models 103, including the patient state models, to reduce the accuracy and/or uncertainty of the models 103 by interacting with one or more medical professionals and the observed interaction data 112. For example, by confirming the above example patient has metastatic prostate cancer, the reinforcement component 107 may retrain the models 103 to reflect that a candidate diagnosis of metastatic prostate cancer was indeed correct based on observed data (e.g., the biopsy confirming the cancer). Furthermore, the reinforcement component 107 may learn new features that are relevant in generating a diagnosis for a patient. For example, the reinforcement component 107 may analyze the data of the patient diagnosed with prostate cancer, to determine that elevated levels of a particular enzyme is correlated with a diagnosis of prostate cancer. As such, the models 103 may be updated to include the enzyme levels as a feature, and feature values for the enzyme may be refined over time to determine the weight applied to the feature when present in the patient data 111. Doing so improves the quality and accuracy of diagnoses and/or treatments generated by the diagnosis system 102.

Figure 2A:
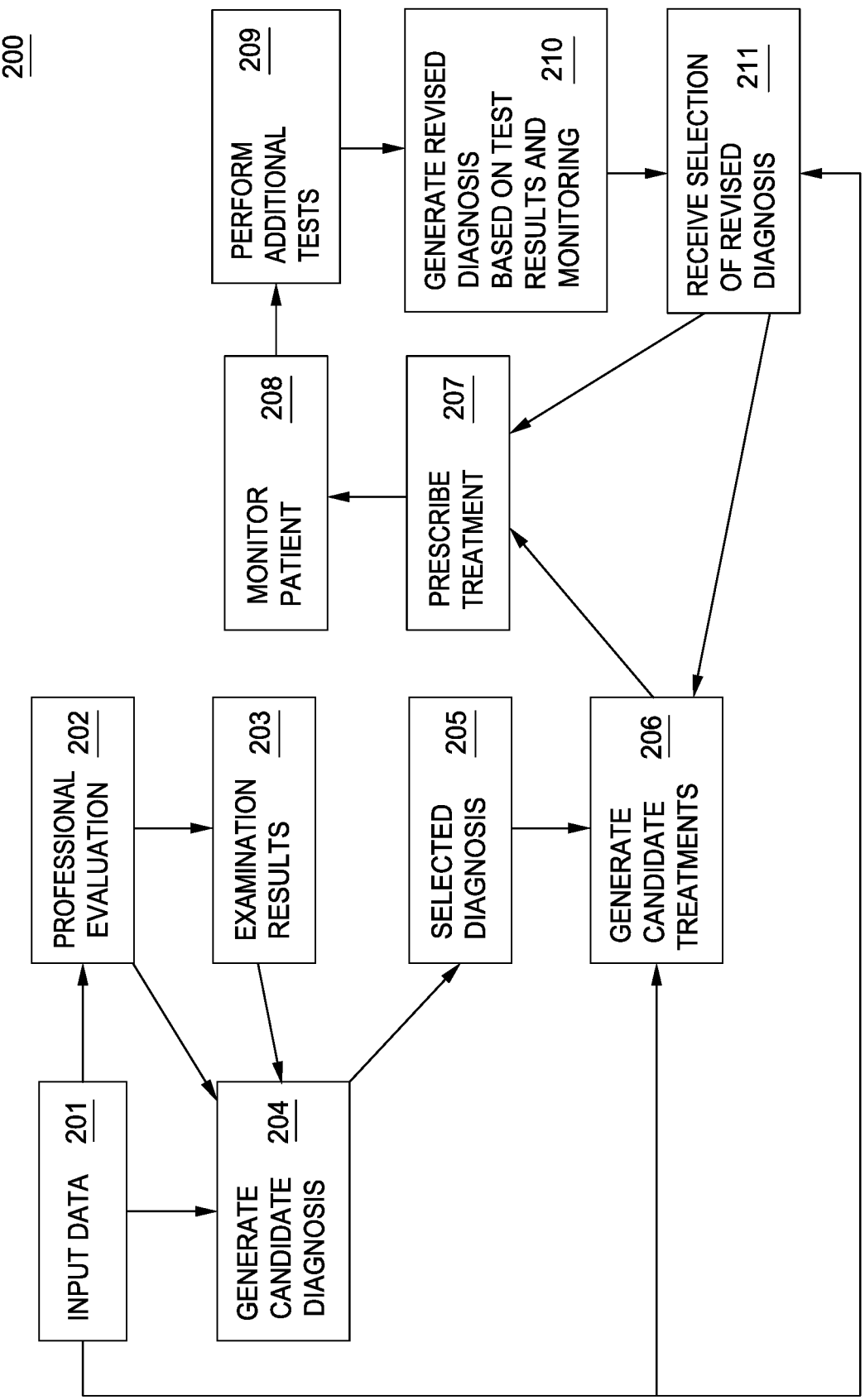
FIGS. 2A-2B illustrate example processes for configuring a medical diagnosis system to perform continuous learning and reasoning, according to one embodiment.

FIG. 2A illustrates an example process 200 for configuring a medical diagnosis system to perform continuous learning and reasoning, according to one embodiment. Generally, the process 200 may be repeatedly performed over time to allow the diagnosis system 102 to generate candidate diagnoses and/or treatments as well as refine the models 103. As shown, the process 200 begins at block 201, where input data is received by the diagnosis system 102 from the data sources $110_{1-N}$. For example, the input data may include patient data 111 (e.g., patient complaints, systems, medical history data, etc.), as well as interaction data 112 (e.g., a recording of a case summary presented by one or more medical professionals), social media data 113 (e.g., a patient's social media data), and/or publication data 114 (e.g., medical literature related to the patient's complaints and/or medical history). At block 202, a medical professional evaluates the patient, generating interaction data 112 that is observed by the diagnosis system 102. For example, the medical professional may dictate notes describing the evaluation of the patient, from which the diagnosis system 102 may extract concepts, grammatical features, and the like. At block 203, results of one or more patient examinations are received (e.g., lab results, ultrasounds, scans, etc.) by the diagnosis system 102. The diagnosis system 102 may generate (or refine) a model 103 for the patient based on the input data, the professional evaluation, and the examination results.

At block 204, the diagnosis system 102 generates one or more candidate diagnoses. The candidate diagnoses may be based on the models 103, the received input data 201, and the data describing the professional evaluation and/or examination results. The diagnosis system 102 may apply the models 103 to the received data to generate one or more candidate diagnoses based on an analysis of a corpus of information (e.g., a knowledge base). In at least one embodiment, the diagnosis system 102 provides a question answering processing pipeline to generate the candidate diagnoses, where the patient's information is the input to the question answering system, and the responses are one or more candidate diagnoses. One example of a question answering system is Watson® by IBM. The diagnosis system 102 may further determine candidate diagnoses using abduction reasoning performed by the reasoning component 106. Generally, abduction reasoning begins with an incomplete set of observations (e.g., the input data 201, the examination results, professional evaluation, etc.), from which the reasoning component 106 determines the most likely explanations (e.g., one or more diagnoses) for the observations. As stated, the diagnosis system 102 computes a score for each candidate diagnosis. In at least one embodiment, the score comprises an uncertainty value associated with the model 103 of the patient relative to an unknown future state of the patient. The candidate diagnoses and computed scores may then be returned to a medical professional, which selects a candidate diagnosis at block 205.

At block 206, the diagnosis system 102 generates one or more candidate treatments based on the models 103 and/or data from the data sources $110_{1-N}$. Generally, the candidate treatments are determined based on the candidate diagnoses, and a plurality of simulations (or emulations) of the treatment may be executed for each candidate treatment relative to the model 103 of the patient. The diagnosis system 102 may further generate the candidate treatments based on a question answering processing pipeline, where the patient information, and candidate diagnoses are the input, and the candidate treatments are returned. The candidate treatments and associated scores may then be outputted to a medical professional, who selects and prescribes a treatment at block 207.

At block 208, the patient is monitored during treatment over a period of time, e.g. days, weeks, months, etc. In some embodiments, the monitoring includes the patient being examined by medical professionals, which may lead to discussions about the patient. As such, the monitoring may generate patient data 111 and/or interaction data 112. At block 209, additional tests are performed on the patient. The diagnosis system 102 may refine the model 103 of the patient based on the continued monitoring, patient data, tests, and interaction data. At block 210, the diagnosis system 102 generates one or more revised diagnoses based on the revised model 103, the results of the tests performed at block 209 and the monitoring of the patient. At block 211, a medical professional selects one or more of the revised diagnoses, and a treatment is prescribed at block 207. In this manner, the patient may be monitored and the diagnosis system 102 may continue to generate candidate diagnoses and treatments. The diagnosis system 102 continues to simulate the application of the treatment to the patient, observing all possible outcomes to converge on the best treatment for the patient.

Figure 2B:
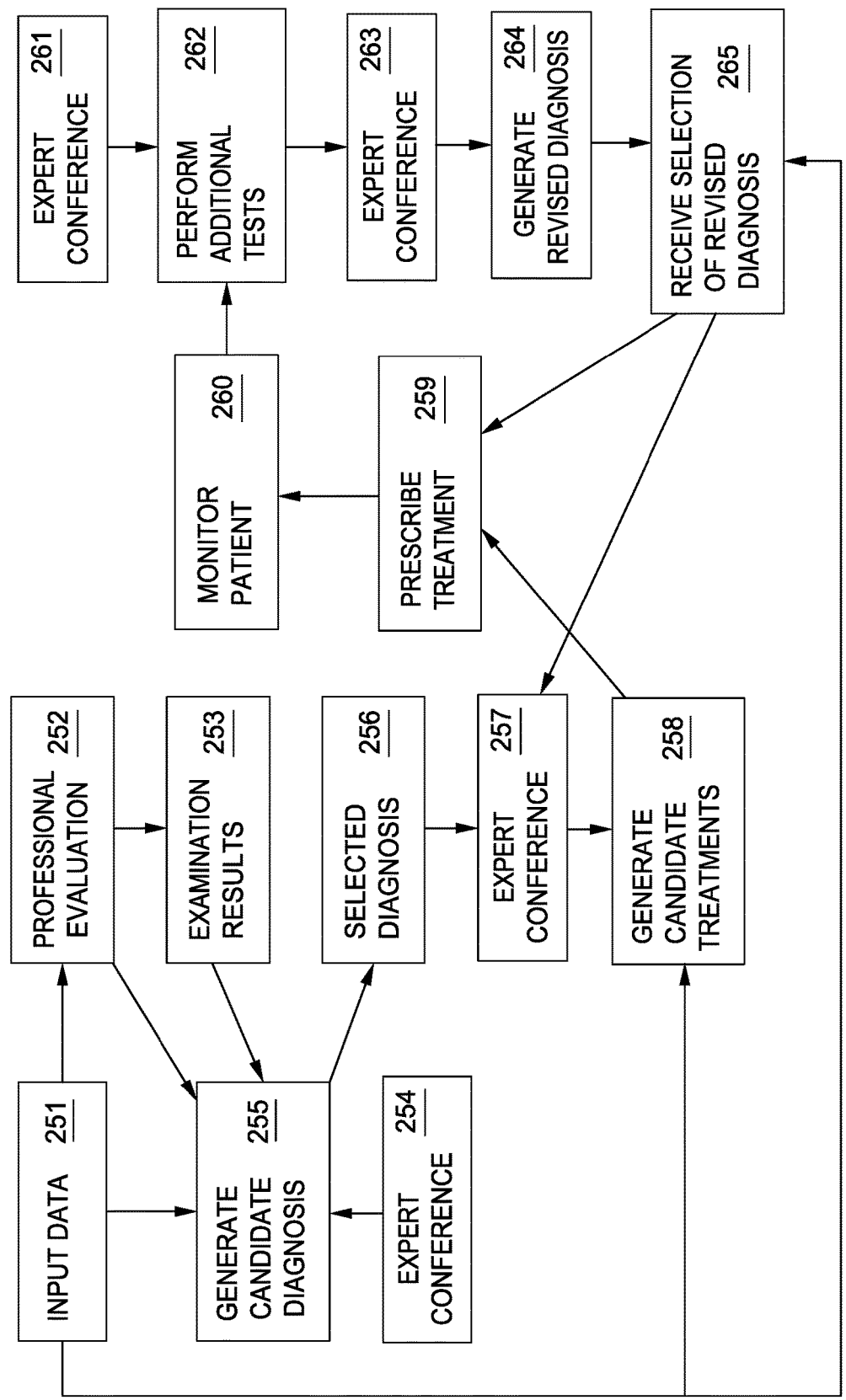

FIG. 2B depicts a process 250 for providing the diagnosis system 102 which performs continuous learning and reasoning, according to one embodiment. As shown, the process 250 begins at block 251, where input data is received by the diagnosis system 102 from the data sources $110_{1-N}$. For example, the input data may include patient data 111 (e.g., patient complaints, systems, medical history data, etc.), as well as interaction data 112 (e.g., a recording of a case summary presented by a medical professional), social media data 113 (e.g., a patient's social media data), and/or publication data 114 (e.g., medical literature related to the patient's complaints and/or medical history). At block 252, a medical professional evaluates the patient, generating interaction data 112 that is observed by the diagnosis system 102. For example, the medical professional may dictate notes describing the evaluation of the patient, from which the diagnosis system 102 may extract concepts, grammatical features, and the like. At block 253, results of one or more patient examinations are received (e.g., lab results, ultrasounds, scans, etc.) by the diagnosis system 102. The diagnosis system 102 may generate (or refine) a model 103 for the patient based on the input data, the professional evaluation, and the examination results.

At block 254, an expert conference is conducted with the diagnosis system 102 present. One example of an expert conference includes one or more physicians discussing the patient with one or more medical residents and the diagnosis system 102, where the diagnosis system 102 receives interaction data 112. The diagnosis system 102 is configured to record the audio of the expert conference via a microphone, perform speech to text conversion of the recorded audio, and apply natural language processing (NLP) algorithms to the converted text. Similarly, the diagnosis system 102 may capture images of the expert conference (which may include images of the patient). The diagnosis system 102 may perform analysis of the images to extract information regarding the patient and/or the conference. Doing so allows the diagnosis system 102 to extract concepts, features, and other data describing the patient, the diagnosis, and treatment options discussed during the expert conference. The diagnosis system 102 may further ask questions during the expert conference. For example, the diagnosis system 102 may ask questions to determine values for missing data elements, such as whether the patient has undergone a specific test, treatment, examination, etc. At block 255, the diagnosis system 102 generates one or more candidate diagnoses based on the patient model 103, input data, professional evaluation, examination results, and the expert conference. As stated, the diagnosis system 102 may generate the candidate diagnoses that minimize the uncertainty in the patient model 103. The diagnosis system 102 may compute uncertainty values for the patient model 103 associated with each candidate diagnosis, which are returned to the medical professional for review.

At block 256, the medical professional selects a diagnosis from the candidate diagnoses, and provides an indication of the selected diagnosis to the diagnosis system 102. At block 257, another expert conference may be conducted to discuss candidate treatments for the patient based on the selected diagnosis. Again, the diagnosis system 102 may receive interaction data 112 related to the treatments during the expert conference. The diagnosis system 102 may also ask questions of the medical professionals during the expert conference. At block 258, the diagnosis system 102 generates one or more candidate treatments based on the expert conference, the input data 251, and the selected diagnosis. The diagnosis system 102 may further simulate each of the treatments based on known effects of each treatment and the model 103 to minimize the uncertainty of the model 103 and minimize the risk outcome for the patient. At block 259, the medical professional prescribes a selected one of the candidate treatments, which are provided to the patient.

At block 260, the patient is monitored over a period of time. At block 261, one or more expert conferences are conducted to discuss the patient monitoring. At block 262, additional tests are performed on the patient. At block 263, an expert conference is conducted to discuss the results of the additional tests and/or the patient monitoring. At block 264, the diagnosis system 102 generates one or more revised diagnoses based on the model 103, expert conferences, patient monitoring, and additional tests. At block 265, the diagnosis system 102 receives selection of a revised diagnosis from a medical professional. The process 250 may then proceed to block 257, where another expert conference is conducted, and revised candidate treatments are generated at block 258. In this manner, the patient may be monitored and the diagnosis system 102 may continue to generate revised candidate diagnoses and treatments as the patient is monitored over time. For example, if the patient initially receives a first treatment, the diagnosis system 102 may determine a month later that the first treatment is not successful. As such, the diagnosis system 102 may generate a revised candidate treatment comprising a second treatment (e.g., a different medication, procedure, test, etc.) based on known risks of each treatment and a plurality of simulations of each treatment. The medical professional may then select the second treatment, which is provided to the patient. Again, the diagnosis system 102 may monitor the patient's condition over time to determine whether the second treatment cures the patient's condition.

Figure 3:
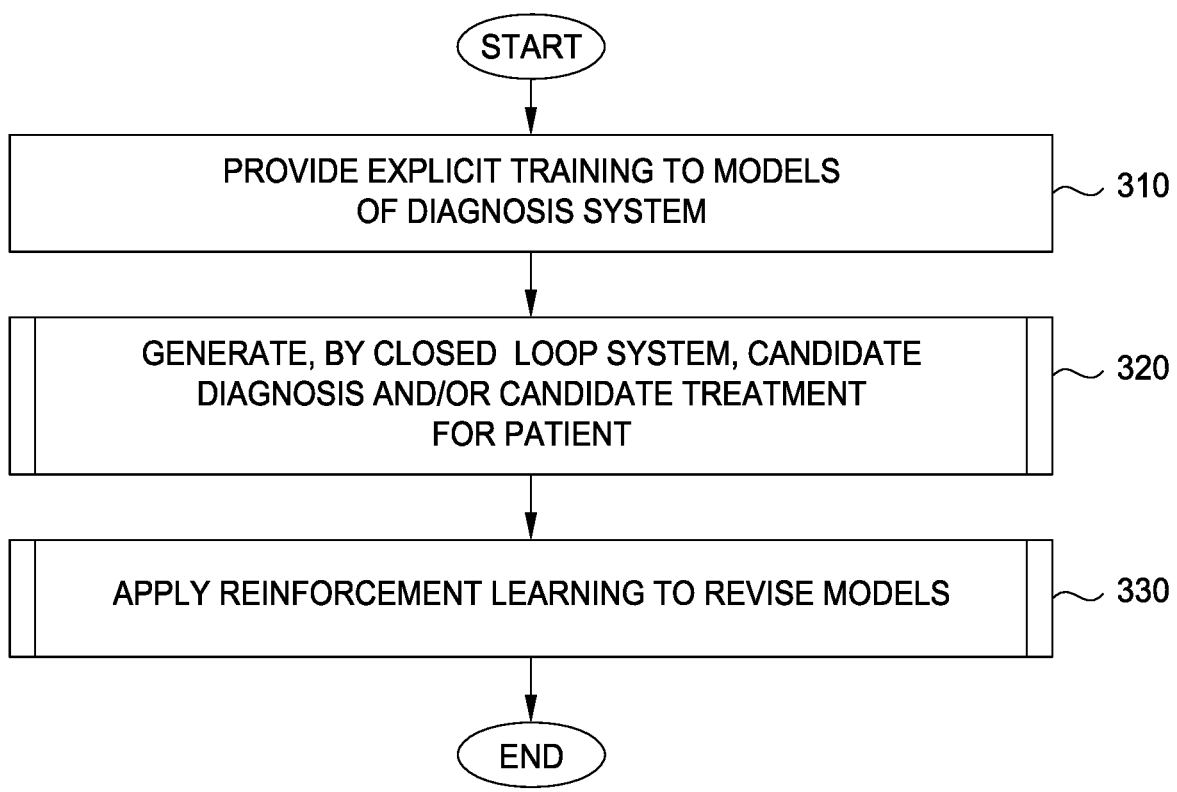
FIG. 3 is a flow chart illustrating a method for providing a medical diagnosis system configured to perform continuous learning and reasoning, according to one embodiment.

FIG. 3 is a flow chart illustrating a method 300 for providing a medical diagnosis system configured to perform continuous learning and reasoning, according to one embodiment. As shown, the method 300 begins at block 310, where the diagnosis system 102 receives explicit training to generate the models 103. The explicit training is based on high-quality historical patient data 111, interaction data 112, social media data 112, and publication data 114. Because the diagnosis system 102 is explicitly trained based on high-quality data, the explicit training occurs faster and using less data relative to explicitly training the diagnosis system 102 without high-quality data. One or more learning algorithms may process the data to generate one or more models 103, which may subsequently be revised and refined using reinforcement learning and new data. At block 320, the diagnosis system 102 may generate a candidate diagnosis and/or a candidate treatment for a patient based on the models 103. For example, the diagnosis system 102 may generate a candidate diagnosis of a heart attack for a patient complaining of chest pains, and prescribe surgery as the candidate treatment for the heart attack. At block 330, the diagnosis system 102 applies reinforcement learning to revise the models 103. For example, if the surgery cures the patient, the diagnosis system 102 retrains the models 103 based on an indication that the surgery was successful for the heart attack patient. However, if the surgery was not successful, the diagnosis system 102 may converge on a new treatment and/or diagnosis for the patient by running a plurality of diagnosis and/or treatment simulations.

Figure 4:
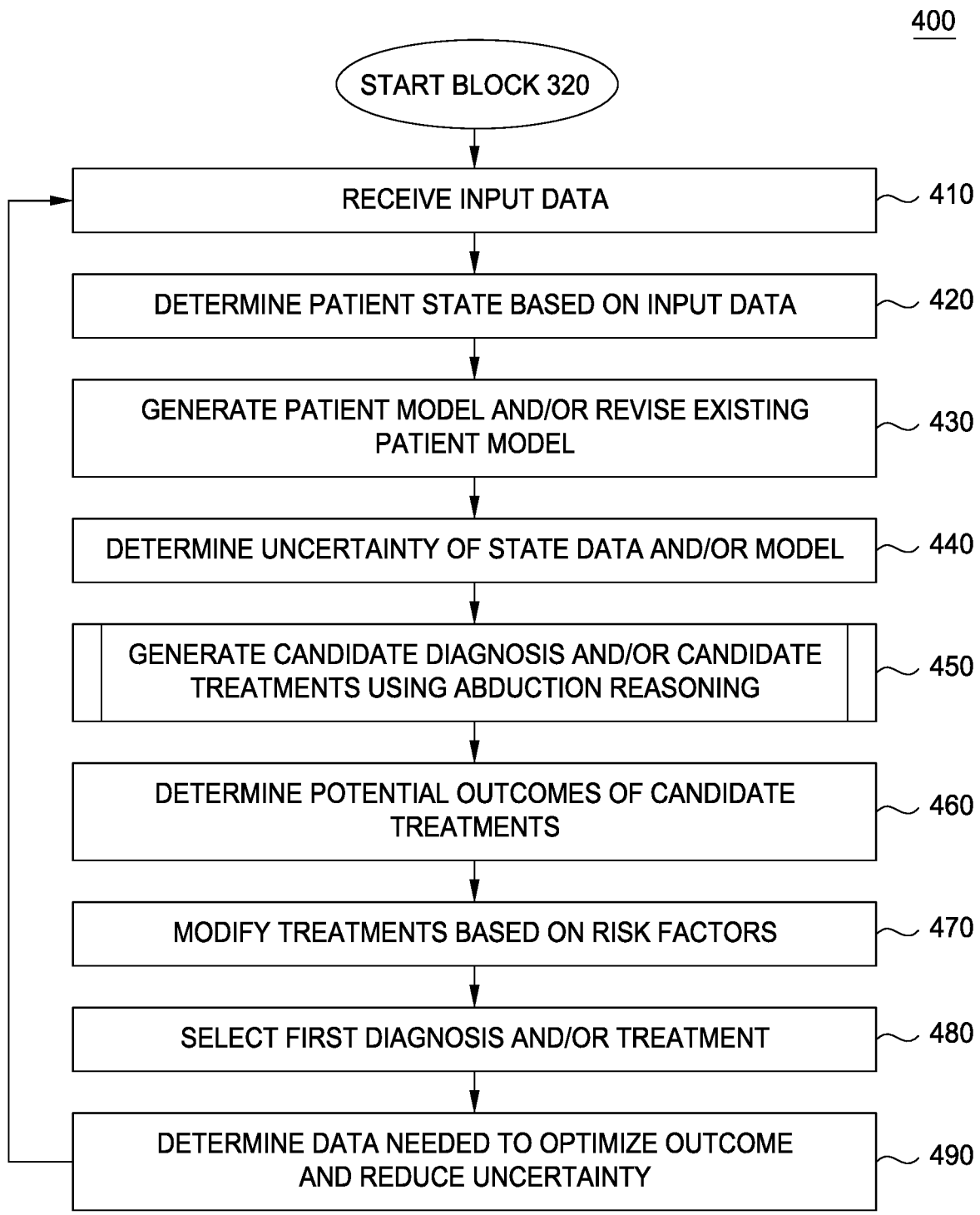
FIG. 4 is a flow chart illustrating a method to generate, by a closed loop system, a candidate diagnosis and/or a candidate treatment for a patient, according to one embodiment.

FIG. 4 is a flow chart illustrating a method 400 corresponding to block 320 to generate, by a closed loop system, a candidate diagnosis and/or a candidate treatment for a patient, according to one embodiment. As shown, the method 400 begins at block 410, where the diagnosis system 102 receives input data from the data sources $110_{1-N}$. The input data includes, without limitation, data describing the patient, e.g., patient history data 111. The diagnosis system 102 may also group patient symptoms, conditions, etc. together to determine a set of possible diagnoses. At block 420, the diagnosis system 102 determines the patient state, e.g., by extracting features from the patient data 111. At block 430, the diagnosis system 102 generates a model 103 for the patient (and/or updates an existing model 103 for the patient) based on the determined patient state. As stated, the model 103 for a patient may include a time series of vectors capturing the patient's state. At block 440, the diagnosis system 102 determines the uncertainty of the state data and/or the model 103, e.g., by determining any unknown parameters, values, features, etc.

At block 450, described in greater detail with reference to FIG. 5, the diagnosis system 102 generates one or more candidate diagnoses and/or candidate treatments using abduction reasoning. At block 460, the diagnosis system 102 conducts simulations to determine the potential outcomes of the generated candidate treatments for the current patient, e.g., to determine potential side effects, risk factors (e.g., complications, contraindications, etc.), and/or outcomes for the patient. At block 470, the diagnosis system 102 modifies the candidate treatments based on the identified risk factors.

For example, if a candidate treatment is determined to include a high likelihood of failure based an identified contraindication, the diagnosis system 102 may compute a low score for the candidate treatment and/or remove the candidate treatment from further consideration. At block 480, a medical professional selects a first candidate diagnosis and/or treatment, and an indication of the selected diagnosis and/or treatment is returned to the diagnosis system 102. At block 490, the diagnosis system 102 determines any data needed to optimize the outcome (e.g., to cure the patient) and reduce uncertainty in the models 103. For example, if additional blood tests are needed, the diagnosis system 102 returns an indication of the needed blood tests to the medical professional, who may order the blood tests. Once performed, the diagnosis system 102 receives the results of the blood tests at block 410. As such, the diagnosis system 102 periodically repeats the steps of the method 400 as new input data is received for the patient. Doing so allows the diagnosis system 102 to revise and refine candidate diagnoses and treatments for the patient over time (e.g., weeks, months, years, etc.).

Figure 5:
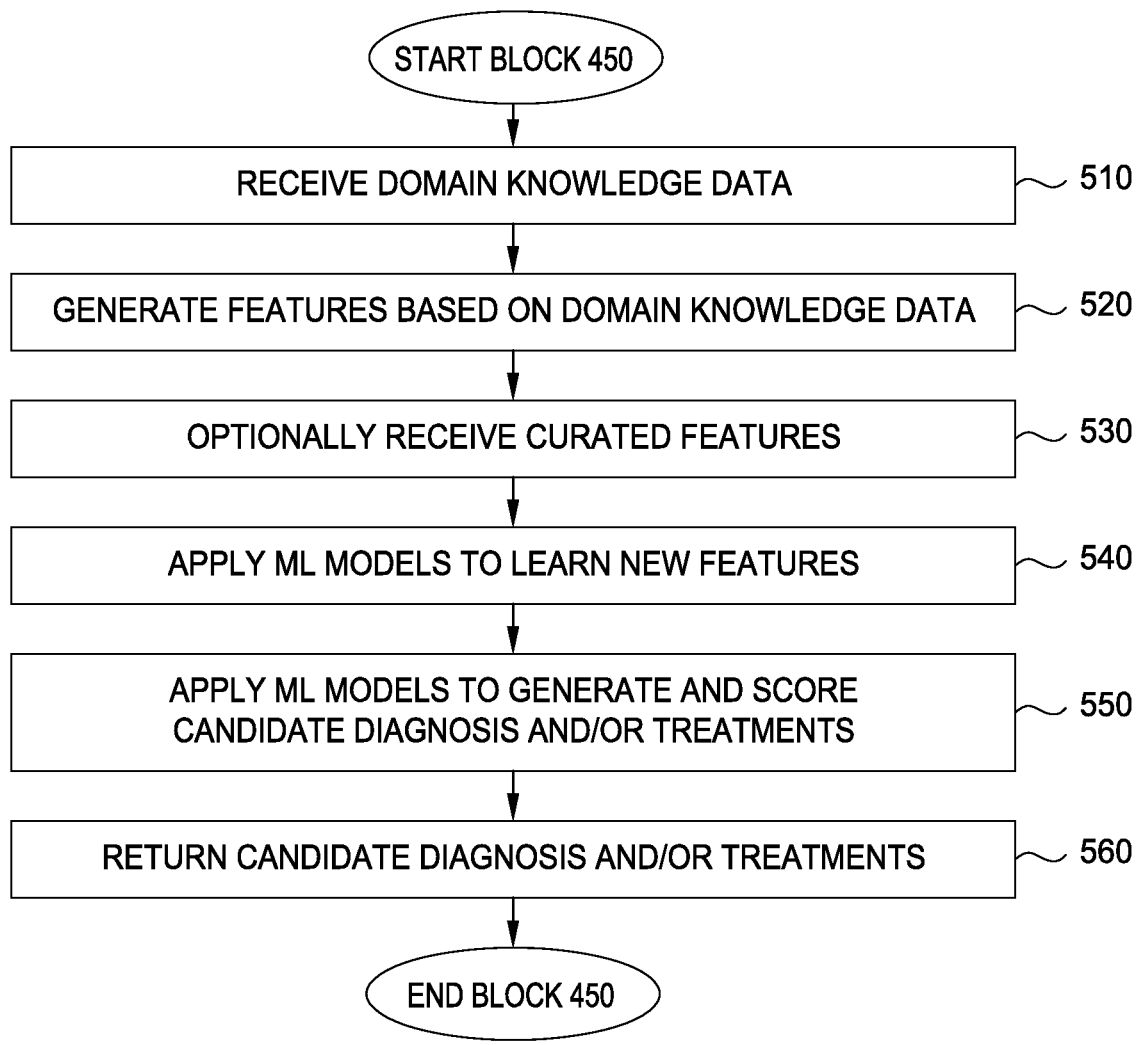
FIG. 5 is a flow chart illustrating a method to generate candidate diagnosis and/or candidate treatments using abduction reasoning, according to one embodiment.

FIG. 5 is a flow chart illustrating a method 500 corresponding to block 450 to generate candidate diagnosis and/or candidate treatments using abduction reasoning, according to one embodiment. As shown, the method 500 begins at block 510, where the diagnosis system 102 receives domain knowledge data. The domain knowledge data may include human generated data and/or machine generated data. For example, the domain knowledge data may include patient history data, speech data, medical texts, images, videos, research articles, social media data, etc. The data may be structured, unstructured, and/or semi-structured data. At block 520, the diagnosis system 102 may optionally generate one or more features, such as patient symptom features, embeddings, and deep learning features generated by learning algorithms. At block 530, the diagnosis system 102 optionally receives curated features, such as a knowledge graph, or other custom features (e.g., 200 day moving average of patient blood tests). At block 540, the diagnosis system 102 applies the models 103 to learn new features and refine existing features. At block 540, the diagnosis system 102 applies the models 103 to generate candidate diagnoses and candidate treatments and compute scores for the generated diagnoses and treatments. At block 560, the diagnosis system 102 returns the scored candidate diagnoses and/or treatments.

Figure 6:
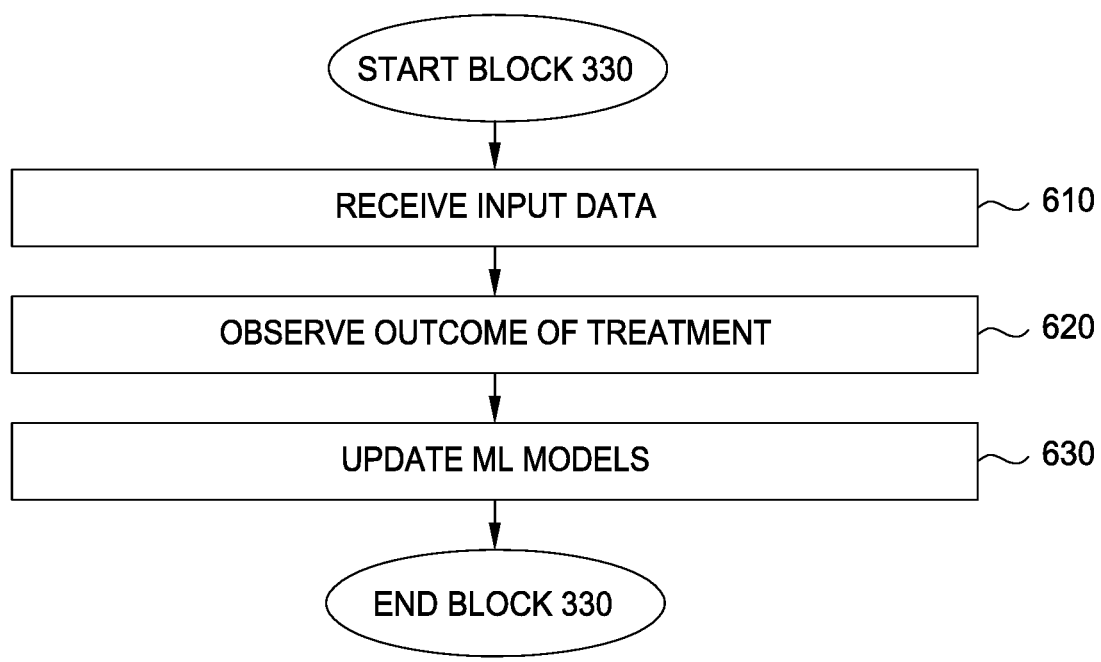
FIG. 6 is a flow chart illustrating a method to apply reinforcement learning to revise machine learning models, according to one embodiment.

FIG. 6 is a flow chart illustrating a method 600 corresponding to block 330 to apply reinforcement learning to revise machine learning models, according to one embodiment. As shown, the method 600 begins at block 610, where the diagnosis system 102 receives input data describing the patient, including any patient history data 111, which may include the candidate diagnoses and/or treatments generated for the patient. At block 620, the diagnosis system 102 observes the outcome of the patient's treatment. For example, the outcome may include updated lab results, notes, and expert conferences discussing the patient's progress and the outcome of the treatment. The diagnosis system 102 may then determine a degree to which the treatment was successful based on the observed data. At block 630, the diagnosis system 102 retrains the models 103 based on the diagnoses, treatments, and the outcomes of the treatments.

Figure 7:
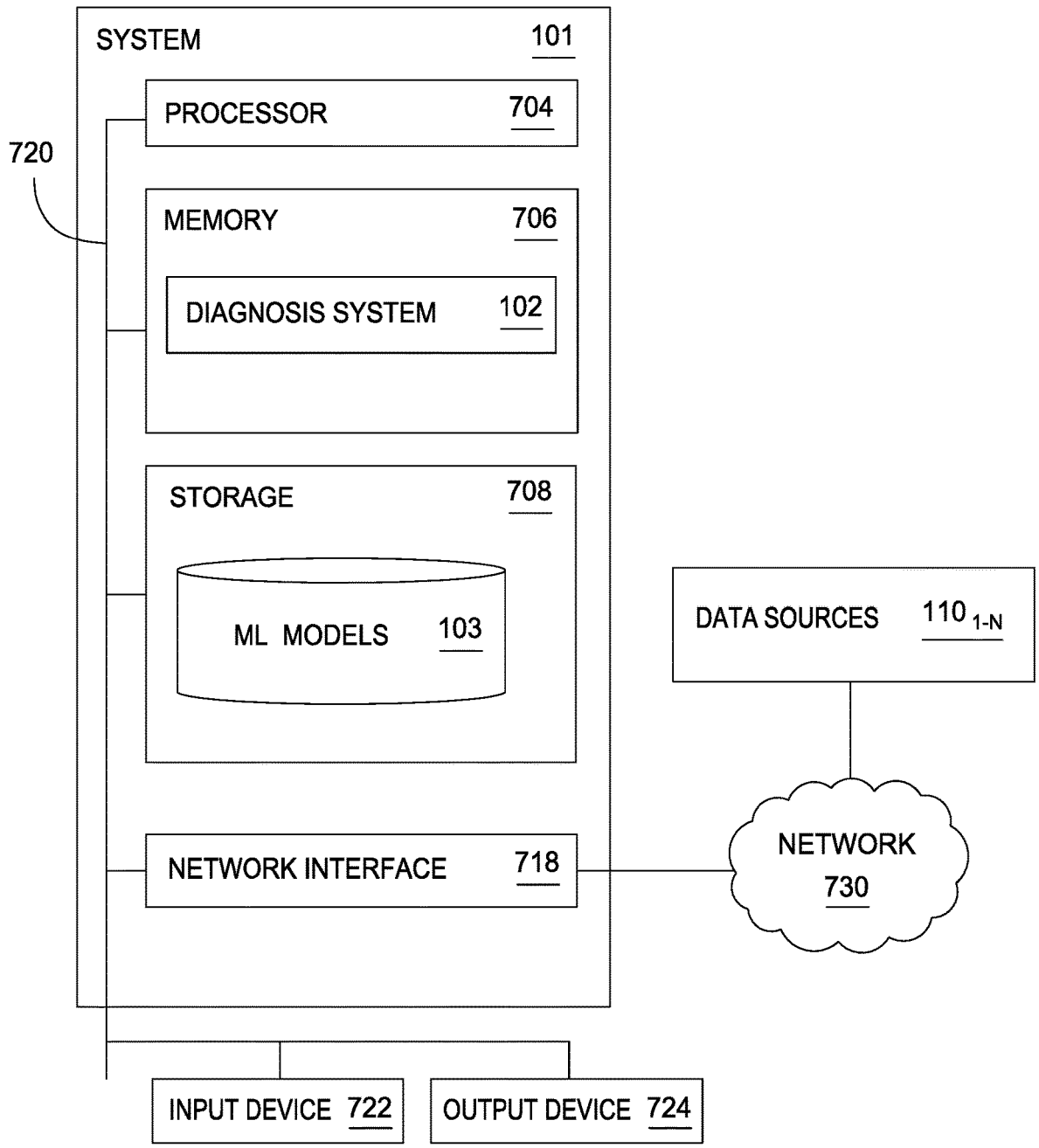
FIG. 7 illustrates a medical diagnosis system configured to perform continuous learning and reasoning, according to one embodiment.

FIG. 7 illustrates a medical diagnosis system 700 configured to perform continuous learning and reasoning, according to one embodiment. The networked system 700 includes the computing system 101. The computing system 101 may also be connected to other computers via a network 730. In general, the network 730 may be a telecommunications network and/or a wide area network (WAN). In a particular embodiment, the network 730 is the Internet.

The computing system 101 generally includes a processor 704 which obtains instructions and data via a bus 720 from a memory 706 and/or a storage 708. The computing system 101 may also include one or more network interface devices 718, input devices 722, and output devices 724 connected to the bus 720. The computing system 101 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 704 is a programmable logic device that performs instruction, logic, and mathematical processing, and may be representative of one or more CPUs. The network interface device 718 may be any type of network communications device allowing the computing system 101 to communicate with other computers via the network 730.

The storage 708 is representative of hard-disk drives, solid state drives, flash memory devices, optical media and the like. Generally, the storage 708 stores application programs and data for use by the computing system 101. In addition, the memory 706 and the storage 708 may be considered to include memory physically located elsewhere; for example, on another computer coupled to the computing system 101 via the bus 720.

The input device 722 may be any device for providing input to the computing system 101. For example, a keyboard and/or a mouse may be used. The input device 722 represents a wide variety of input devices, including cameras, microphones, keyboards, mice, controllers, and so on. Furthermore, the input device 722 may include a set of buttons, switches or other physical device mechanisms for controlling the computing system 101. The output device 724 may include output devices such as monitors, speakers, touch screen displays, and so on.

As shown, the memory 706 contains diagnosis system 102, described in greater detail above. As shown, the storage 708 contains the models 103, described in greater detail above. Generally, the system 700 is configured to implement all systems, methods, and functionality described above with reference to FIGS. 1-6.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the diagnosis system 102 could execute on a computing system in the cloud and generate candidate diagnoses and/or treatments. In such a case, the diagnosis system 102 could store indications of the candidate diagnoses and/or treatments at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   generating, by a computing system based on data received from a plurality of data sources, a data model describing a patient, wherein:
   the data comprises medical history data of the patient and observation data received by the computing system during observation of at least one medical professional,
   the observation data comprises: (i) audio data recorded by a microphone of the computing system, and (ii) image data captured by a camera of the computing system, and
   the data model comprises a sequence of vectors collected over time, each respective vector in the sequence of vectors capturing attributes of the patient for a respective time;

generating, by the computing system and based on the data model applied to the received data, a plurality of candidate diagnoses for the patient by applying abductive reasoning to reduce uncertainty in the data model, wherein the uncertainty is based on unknown data in the data model;

generating, for each respective candidate diagnosis of the plurality of candidate diagnoses, a respective score reflecting confidence the respective diagnosis reduces uncertainty in the data model;

executing, by the computing system, for a plurality of candidate treatments, a respective plurality of simulations based on the data model, comprising determining predicted uncertainties with respect to a future state of the data model; and identifying a first candidate treatment of the plurality of candidate treatments based on the respective plurality of simulations executed for the first candidate treatment, comprising determining that the first candidate treatment reduces the predicted uncertainty of the future state of the data model below a threshold.

2. The method of claim 1, wherein generating the plurality of candidate diagnoses is further based on: (i) an evaluation of the patient performed by the medical professional, (ii) results of a plurality of patient examinations, (iii) medical literature, and (iv) social media data.

3. The method of claim 2, further comprising:
receiving selection of a first candidate diagnosis of the plurality of candidate diagnoses;
computing a score for each of the candidate treatments;
outputting the candidate treatments and the computed scores for display;
receiving selection of the first candidate treatment; and
determining at least one unspecified data element needed to improve an accuracy of the first candidate treatment.

4. The method of claim 3, further comprising:
receiving data describing an outcome of the first candidate treatment for the patient; and
retraining the data model based on the outcome of the first candidate treatment, the first candidate diagnosis, and the plurality of simulations.

5. The method of claim 4, wherein the data model comprises a plurality of features, wherein retraining the data model comprises identifying a new feature by a learning algorithm.

6. The method of claim 1, further comprising:
receiving updated patient state data;
generating, by the system based on the data model applied to the updated patient state data, a revised candidate diagnosis; and
generating, by the system based on the data model applied to the updated patient state data and the revised candidate diagnosis, a revised candidate treatment.

7. The method of claim 6, further comprising:
generating the data model based on the patient state data, wherein the data model comprises a plurality of vectors describing a plurality of features of the patient state.

8. A computer program product, comprising:
a non-transitory computer-readable storage medium having computer readable program code embodied therewith, the computer readable program code executable by a processor to perform an operation comprising:
generating, by a computing system based on data received from a plurality of data sources, a data model describing a patient, wherein:
the data comprises medical history data of the patient and observation data received by the computing system during observation of at least one medical professional,
the observation data comprises: (i) audio data recorded by a microphone of the computing system, and (ii) image data captured by a camera of the computing system, and
the data model comprises a sequence of vectors collected over time, each respective vector in the sequence of vectors capturing attributes of the patient for a respective time;
generating, by the computing system and based on the data model applied to the received data, a plurality of candidate diagnoses for the patient by applying abductive reasoning to reduce uncertainty in the data model, wherein the uncertainty is based on unknown data in the data model;
generating, for each respective candidate diagnosis of the plurality of candidate diagnoses, a respective score reflecting confidence the respective diagnosis reduces uncertainty in the data model;
executing, by the computing system, for a plurality of candidate treatments, a respective plurality of simulations based on the data model, comprising determining predicted uncertainties with respect to a future state of the data model; and
identifying a first candidate treatment of the plurality of candidate treatments based on the respective plurality of simulations executed for the candidate first treatment, comprising determining that the first candidate treatment reduces the predicted uncertainty of the future state of the data model below a threshold.

9. The computer program product of claim 8, wherein generating the plurality of candidate diagnoses is further based on: (i) an evaluation of the patient performed by the medical professional, (ii) results of a plurality of patient examinations, (iii) medical literature, and (iv) social media data.

10. The computer program product of claim 9, the operation further comprising:
receiving selection of a first candidate diagnosis of the plurality of candidate diagnoses;
computing a score for each of the candidate treatments;
outputting the candidate treatments and the computed scores for display;
receiving selection of the first candidate treatment; and
determining at least one unspecified data element needed to improve an accuracy of the first candidate treatment.

11. The computer program product of claim 10, the operation further comprising:
receiving data describing an outcome of the first candidate treatment for the patient; and
retraining the data model based on the outcome of the first candidate treatment, the first candidate diagnosis, and the plurality of simulations.

12. The computer program product of claim 11, wherein the data model comprises a plurality of features, wherein retraining the data model comprises identifying a new feature by a learning algorithm.

13. The computer program product of claim 8, the operation further comprising:
receiving updated patient state data;
generating, by the system based on the data model applied to the updated patient state data, a revised candidate diagnosis; and generating, by the system based on the data model applied to the updated patient state data and the revised candidate diagnosis, a revised candidate treatment.

14. The computer program product of claim 13, the operation further comprising:
generating the data model based on the patient state data, wherein the data model comprises a plurality of vectors describing a plurality of features of the patient state.

15. A system, comprising:
a processor; and
a memory storing one or more instructions which, when executed by the processor, performs an operation comprising:
generating, by the system based on data received from a plurality of data sources, a data model describing a patient, wherein:
the data comprises medical history data of the patient and observation data received by the computing system during observation of at least one medical professional,
the observation data comprises: (i) audio data recorded by a microphone of the computing system, and (ii) image data captured by a camera of the computing system, and
the data model comprises a sequence of vectors collected over time, each respective vector in the sequence of vectors capturing attributes of the patient for a respective time;
generating, by the system and based on the data model applied to the received data, a plurality of candidate diagnoses for the patient by applying abductive reasoning to reduce uncertainty in the data model, wherein the uncertainty is based on unknown data in the data model;
generating, for each respective candidate diagnosis of the plurality of candidate diagnoses, a respective score reflecting confidence the respective diagnosis reduces uncertainty in the data model;
executing, by the system, for a plurality of candidate treatments, a respective plurality of simulations based on the data model, comprising determining predicted uncertainties with respect to a future state of the data model; and
identifying a first candidate treatment of the plurality of candidate treatments based on the respective plurality of simulations executed for the first candidate treatment, comprising determining that the first candidate treatment reduces the predicted uncertainty of the future state of the data model below a threshold.

16. The system of claim 15, wherein generating the plurality of candidate diagnoses is further based on: (i) an evaluation of the patient performed by the medical professional, (ii) results of a plurality of patient examinations, (iii) medical literature, and (iv) social media data.

17. The system of claim 16, the operation further comprising:
receiving selection of a first candidate diagnosis of the plurality of candidate diagnoses;
computing a score for each of the candidate treatments;
outputting the candidate treatments and the computed scores for display;
receiving selection of the first candidate treatment; and
determining at least one unspecified data element needed to improve an accuracy of the first candidate treatment.

18. The system of claim 17, the operation further comprising:
receiving data describing an outcome of the first candidate treatment for the patient; and
retraining the data model based on the outcome of the first candidate treatment, the first candidate diagnosis, and the plurality of simulations.

19. The system of claim 18, wherein the data model comprises a plurality of features, wherein retraining the data model comprises identifying a new feature by a learning algorithm.

20. The system of claim 15, the operation further comprising:
receiving updated patient state data;
generating, by the system based on the data model applied to the updated patient state data, a revised candidate diagnosis; and
generating, by the system based on the data model applied to the updated patient state data and the revised candidate diagnosis, a revised candidate treatment.

* * * * *